US00PP21515P2

(12) United States Plant Patent
Brugliera

(10) Patent No.: US PP21,515 P2
(45) Date of Patent: Nov. 23, 2010

(54) ***DIANTHUS* PLANT NAMED 'FLORIJADE'**

(50) Latin Name: *Dianthus caryophyllus*
Varietal Denomination: Florijade

(75) Inventor: Filippa Brugliera, Preston (AU)

(73) Assignee: International Flower Developments Pty Ltd., Bundoora, Victoria (AU)

( * ) Notice: Subject to any disclaimer, the term of this patent is extended or adjusted under 35 U.S.C. 154(b) by 0 days.

(21) Appl. No.: 12/454,905

(22) Filed: May 26, 2009

(51) Int. Cl.
*A01H 5/00* (2006.01)

(52) U.S. Cl. ..... Plt./278

(58) Field of Classification Search ..... Plt./278, Plt./273
See application file for complete search history.

(56) References Cited

FOREIGN PATENT DOCUMENTS

| | | |
|---|---|---|
| WO | WO 93/01290 | 1/1993 |
| WO | WO 96/36716 | 11/1996 |
| WO | WO 2004/020637 A1 | 3/2004 |

OTHER PUBLICATIONS

Dellaporta et al, "A Plant DNA Minipreparation: Version II," *Molecular Biology Reporter 1* (*14*):19-21, 1983.
De Vetten et al, "A cytochrom $b_5$*is required for full activity of flavonoid3', 5'—hydroxylase, a cytochrome P450 involved in the formation of blue flower colors," Proc. Nati. Acad. Sci. USA,* vol. 96, pp. 778-783, 1999, Plant Biology.
Forkmann and Ruhnau, "Distinct Substrate Specificity of Dihydroflavonol 4-Reductase from Flowers of Petunia hybrida," *Z Naturforsch C.* 42c, 1146-1148, 1987.
Holton et al, "Cloning and expression of cytochrome P450 genes controlling flower colour," *Nature, 366*: 276-279, 1993.
Holton and Cornish, "Genetics and Biochemistry of Anthocyanin Biosynthesis," *Plant Cell 7*:1071-1083, 1995.
Johnson et al, "*Cymbidium hybrida dihydroflavonol* 4-reductase does not efficiently reduce dihydrokaempferol to produce orange pelargonidin-type anthocyanins,", *Plant Journal, 19*, 81-85, 1999.
Lazo et al, "A DNA Transformation-Competent Arabidopsis Genomic Library in Agrobacterium," *Bio/technology 9*:963-967, 1991.
Lu et al, "Agrobacterium-Mediated Transformation of Carnation (*Dianthus Caryophyllus L.*)," *Bio/Technology 9*: 864-868, 1991.
Mol et al, "How Genes Paint Flowers and Seeds," *Trends Plant Sci. 3*:212-217, 1998.
Sambrook et al, "Molecular Cloning: A Laboratory Manual," Cold Spring Harbor Laboratories, Cold Spring Harbor, NY, USA, 1989.
Tanaka and Mason, "Manipulation of Flower Colour by Genetic Engineering," Chapter 15, In *Plant Genetic Engineering*, Singh and Jaiwal (eds) SciTech Publishing LLC., USA, 1: 361-385, 2003.
Tanaka et al, "Genetic Engineering in Floriculture," *Plant Cell, Tissue and Organ Culture 80*: 1—24, 2005.
Tanaka and Brugliera, "Flower colour," Chapter 9, *In Flowering and Its Manipulation, Annual Plant Reviews* Ainsworth (ed), Blackwell Publishing, UK,20: 201-239, 2006.
Winkel-Shirley, "Flavinoid Biosynthesis. A Colorful Model for Genetics, Biochemistry, Cell Biology, and Biotechnology," *Plant Physiol. 126*:485-493, 2001a.
Winkel-Shirley, "It Takes a Garden. How Work on Diverse Plant Species has Contributed to an Understanding of Flavonoid Metabolism," *Plant Physiol. 127*:1399-1404, 2001b.

*Primary Examiner*—Susan B McCormick Ewoldt
(74) *Attorney, Agent, or Firm*—Knobbe, Martens, Olson & Bear LLP

(57) ABSTRACT

A new cultivar of *Dianthus* plant named 'FLORIJADE' is characterized, inter alia, by pronounced spray habit, perennial and profuse bloom, and green foliage. *Dianthus* 'FLORIJADE' is suitable for use, for example, as a flowering plant in pots, containers, window boxes, and the garden, but is primarily suited for the production of cut flowers. *Dianthus* 'FLORIJADE' is not hardy and is typically grown in a glasshouse. These traits set 'FLORIJADE' apart from all existing varieties, lines, strains, or sports of *Dianthus*. In particular, *Dianthus* 'FLORIJADE' has bright purple/violet flowers.

3 Drawing Sheets

Latin name of the genus and species claimed: *Dianthus caryophyllus.*
Variety denomination: 'FLORIJADE'.

FIELD OF THE INVENTION

A new cultivar of *Dianthus* plant named 'FLORIJADE' that is characterized, inter alia, by altered inflorescence in respect of tissue and/or organelles including flowers or flower parts. This trait sets 'FLORIJADE' apart from all other existing varieties, lines, strains or sports of *Dianthus*. In particular, *Dianthus* 'FLORIJADE' has bright purple/violet flowers.

BACKGROUND OF THE INVENTION

The flower or ornamental plant industry strives to develop new and different varieties of flowers and/or plants. An effective way to create such novel varieties is through the manipulation of flower color. Classical breeding techniques have been used with some success to produce a wide range of colors for almost all of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such as flowers, foliage and stems would offer a significant opportunity in both the cut flower and ornamental markets. In the flower or ornamental plant industry, the development of desired (including novel) colored varieties of carnation is of particular interest. This includes not only different colored flowers but also anthers and styles.

Flower color is predominantly due to three types of pigment: flavonoids, carotenoids and betalains. Of the three, the flavonoids are the most common and contribute a range of colors from yellow to red to blue. The flavonoid molecules that make the major contribution to flower color are the anthocyanins, which are glycosylated derivatives of cyanidin and its methylated derivative peonidin, delphinidin and its methylated derivatives petunidin and malvidin and pelargonidin. Anthocyanins are localized in the vacuole of the epidermal cells of petals or the vacuole of the sub epidermal cells of leaves.

The flavonoid pigments are secondary metabolites of the phenylpropanoid pathway. The biosynthetic pathway for the flavonoid pigments (flavonoid pathway) is well established, (Holton and Cornish, Plant Cell 7:1071-1083, 1995; Mol et al, Trends Plant Sci. 3:212-217, 1998; Winkel-Shirley, Plant Physiol. 126:485-493, 2001a; and Winkel-Shirley, Plant Physiol. 127:1399-1404, 2001b, Tanaka and Mason, In Plant Genetic Engineering, Singh and Jaiwal (eds) SciTech Publishing Llc., USA, 1: 361-385, 2003, Tanaka et al, Plant Cell, Tissue and Organ Culture 80: 1-24, 2005, Tanaka and Brugliera, In Flowering and Its Manipulation, Annual Plant Reviews Ainsworth (ed), Blackwell Publishing, UK, 20: 201-239, 2006). Three reactions and enzymes are involved in the conversion of phenylalanine to p-coumaroyl-CoA, one of the first key substrates in the flavonoid pathway. The enzymes are phenylalanine ammonia-lyase (PAL), cinnamate 4-hydroxylase (C4H) and 4-coumarate: CoA ligase (4CL). The first committed step in the pathway involves the condensation of three molecules of malonyl-CoA (provided by the action of acetyl CoA carboxylase (ACC) on acetyl CoA and CO2) with one molecule of p-coumaroyl-CoA. This reaction is catalyzed by the enzyme chalcone synthase (CHS). The product of this reaction, 2',4,4',6', tetrahydroxy-chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The pattern of hydroxylation of the B-ring of DHK plays a key role in determining petal color. The B-ring can be hydroxylated at either the 3', or both the 3' and 5' positions, to produce dihydroquercetin (DHQ) or dihydromyricetin (DHM), respectively. Two key enzymes involved in this part of the pathway are flavonoid 3'-hydroxylase (F3'H) and flavonoid 3', 5'-hydroxylase (F3'5'H), both members of the cytochrome P450 class of enzymes.

The production of colored anthocyanins from the dihydroflavonols (DHK, DHQ, DHM), involves dihydroflavonol-4-reductase (DFR) leading to the production of the leucoanthocyanidins. The leucoanthocyanidins are subsequently converted to the anthocyanidins, pelargonidin, cyaniding, and delphinidin. These flavonoid molecules are unstable under normal physiological conditions and glycosylation at the 3-position, through the action of glycosyltransferases, stabilizes the anthocyanidin molecule thus allowing accumulation of the anthocyanins.

Nucleotide sequences encoding F3'5'Hs have been cloned (see International Patent Application No. PCT/AU92/00334, incorporated herein by reference, Holton et al, Nature, 366: 276-279, 1993, and International Patent Application No. PCT/AU03/01111, incorporated herein by reference). These sequences were efficient in modulating 3', 5' hydroxylation of flavonoids in petunia (see International Patent Application No. PCT/AU92/00334 and Holton et al, 1993 supra), tobacco (see International Patent Application No. PCT/AU92/00334), carnations (see International Patent Application No. PCT/AU96/00296, incorporated herein by reference), and roses (see International Patent Application No. PCT/AU03/01111).

Cytochrome b5 proteins(Cyt b5) are common to animals, plants and yeast (De Vetten et. al., 1999). Experiments show that Cyt b5 can accept electrons from either NADH-cytochrome reductase or NADPH-Cyt P450 reductase and donate electrons to different desaturases involved in lipid biosynthesis and/or to members of the Cyt P450 superfamily. In 1999, De Vetten et. al. demonstrated that Cyt b5 was required for the full activity of petunia F3'5'H in vivo and therefore for the generation of purple/blue flower colors in petunia.

Carnations are one of the most extensively grown cut flowers in the world.

There are thousands of current and past cut-flower varieties of cultivated carnation. These are divided into three general groups based on plant form, flower size, and flower type. The three flower types are standards, sprays, and midis. Most of the carnations sold fall into two main groups, the standards and the sprays. Standard carnations are intended for cultivation under conditions in which a single large flower is required per stem. Side shoots and buds are removed (a process called disbudding) to increase the size of the terminal flower. Sprays and/or miniatures are intended for cultivation to give a large number of smaller flowers per stem. Only the central flower is removed, allowing the laterals to form a 'fan' of flowers.

Spray carnation varieties are popular in the floral trade, as the multiple flower buds on a single stem are well suited to various types of flower arrangements and provide bulk to bouquets used in the mass market segment of the industry.

Standard and spray cultivars dominate the carnation cut-flower industry, with approximately equal numbers sold of each type in the USA. In Japan, Spray-type varieties account for 70% of carnation flowers sold by volume, whilst in Europe spray-type carnations account for approximately 50% of carnation flowers traded through out the Dutch auctions. The Dutch auction trade is a good indication of consumption across Europe.

While standard and midi-type carnations have been successfully manipulated genetically to introduce new colors (Tanaka and Brugliera, 2006, supra; see International Patent Application No. PCT/AU96/00296), this has not been applied to spray carnations. There is an absence of blue color in color-assortment in carnation, only recently filled through the introduction of genetically-modified standard-type carnation varieties. However, standard-type varieties cannot be used for certain purposes, such as bouquets and flower arrangements where a large number of smaller carnation flowers are needed, such as hand-held arrangements and small table settings.

One particular spray carnation which is particularly commercially popular is the Cerise Westpearl line of carnations (*Dianthus caryophyllus* cv. Cerise Westpearl). The variety has excellent growing characteristics and a moderate to good resistance to fungal pathogens such as *Fusarium*.

SUMMARY OF THE INVENTION

The following traits represent the characteristics of the new *Dianthus* cultivar 'FLORIJADE'. These traits distinguish this cultivar from other commercial varieties. 'FLORIJADE' may exhibit phenotypic differences with variations in environmental, climatic, and cultural conditions, without any variance in genotype.

1. *Dianthus* 'FLORIJADE' exhibits pronounced spray habit.

2. *Dianthus* 'FLORIJADE' blooms profusely.
3. *Dianthus* 'FLORIJADE' exhibits bright purple/violet flowers (RHS N78A).
4. *Dianthus* 'FLORIJADE' exhibits green (RHS 137A) foliage.
5. At maturity, the height of the foliage mound of *Dianthus* 'FLORIJADE' is about 93 cm. The mature width is about 15 to 18 cm.
6. *Dianthus* 'FLORIJADE' is an herbaceous perennial.
7. *Dianthus* 'FLORIJADE' is suitable for a use as a flowering plant in pots, containers, window boxes, and the garden, but is primarily suited for the production of cut flowers.
8. *Dianthus* 'FLORIJADE' is not hardy and is grown in a glasshouse.

BRIEF DESCRIPTION OF THE DRAWINGS

The accompanying color drawings illustrate the overall appearance of the new variety *Dianthus* 'FLORIJADE' showing colors as true as reasonably possible to obtain in colored reproductions of this type. Colors in the drawings may differ from the color values cited in the detailed botanical description, which accurately describes the actual colors of the new variety 'FLORIJADE'.

DETAILED DESCRIPTION OF THE PREFERRED EMBODIMENT

The present invention relates to a new and distinct cultivar of carnation that is grown for use, for example, as a flowering plant for pots and containers. The new cultivar is known botanically as *Dianthus caryophyllus* and is referred to hereinafter by the cultivar name 'FLORIJADE'.

'FLORIJADE' is a complex transgenic plant comprising a functional F3',5'H and a cytochrome b5 in petals. The vector pCGP2355 used to transform meristematic cells contained the carnANS 5': pet F3'5'H: carnANS 3' expression cassette along with a AmCHS 5': pet cytb5: petD8 3' expression cassette and the 35S 5': SuRB selectable marker gene cassette of the plasmid pWTT2132.

The new variety originated in vitro by *Agrobacterium tumefaciens*-mediated transformation of meristematic cells of the Cerise Westpearl carnation with the pCGP2355 vector at Florigene Pty Ltd, in Bundoora, Victoria, Australia. Cuttings of *Dianthus caryophyllus* cv. Cerise Westpearl were obtained from Propagation Australia, Queensland, Australia. Transgenic plants containing a chimeric petunia F3'5'H gene in tandem with a petunia cytochrome b5 gene were successfully generated from the cells. In addition to these genes, the plants also contained genes for acetolactate synthase resistance (SuRB) transformation selection markers. The transformation and regeneration process is described in International Patent Application No. PCT/US92/02612; International Patent Application No. PCT/AU96/00296; and Lu et al, Bio/Technology 9: 864-868, 1991, the contents of each are herein incorporated by reference.

The primary focus of the carnation generation program was to produce new cultivars of carnations, which exhibited a selected and desired purple/violet color in the spray background. The term 'FLORIJADE' was selected because of its pronounced production of delphinidin or delphinidin-based pigments.

The new variety was selected from a group of 47 transgenic lines. 'FLORIJADE' is essentially similar to the parent in the morphological aspects of the flower, but can be distinguished from the parent through out based on the accumulation of the purple delphinidin-based pigment in the petals of the flower. This is a new phenotype of the transgenic line.

Figure 1:
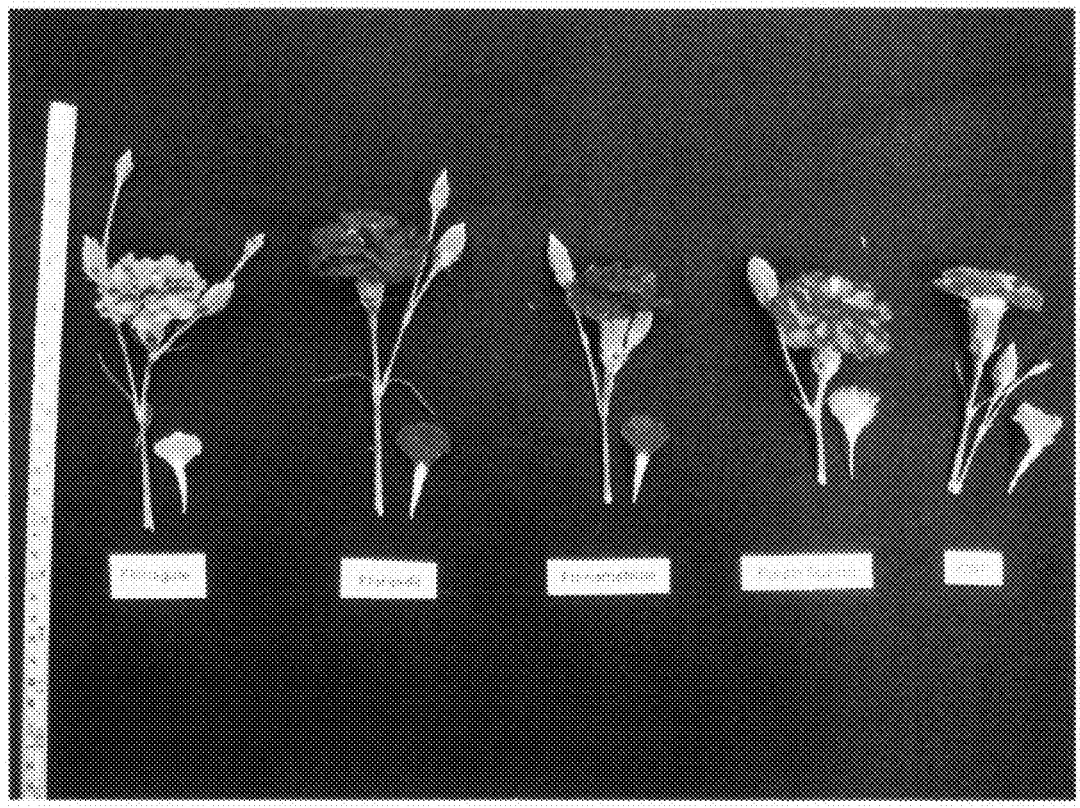
FIG. 1 is a photographic representation of the flower in comparison with other known *dianthus* cultivars. Please note that 'CWP' stands for 'Cerise Westpearl'. Colors may appear different from the actual colors due to light reflection but are as accurate as possible by conventional photography.
Figure 2:
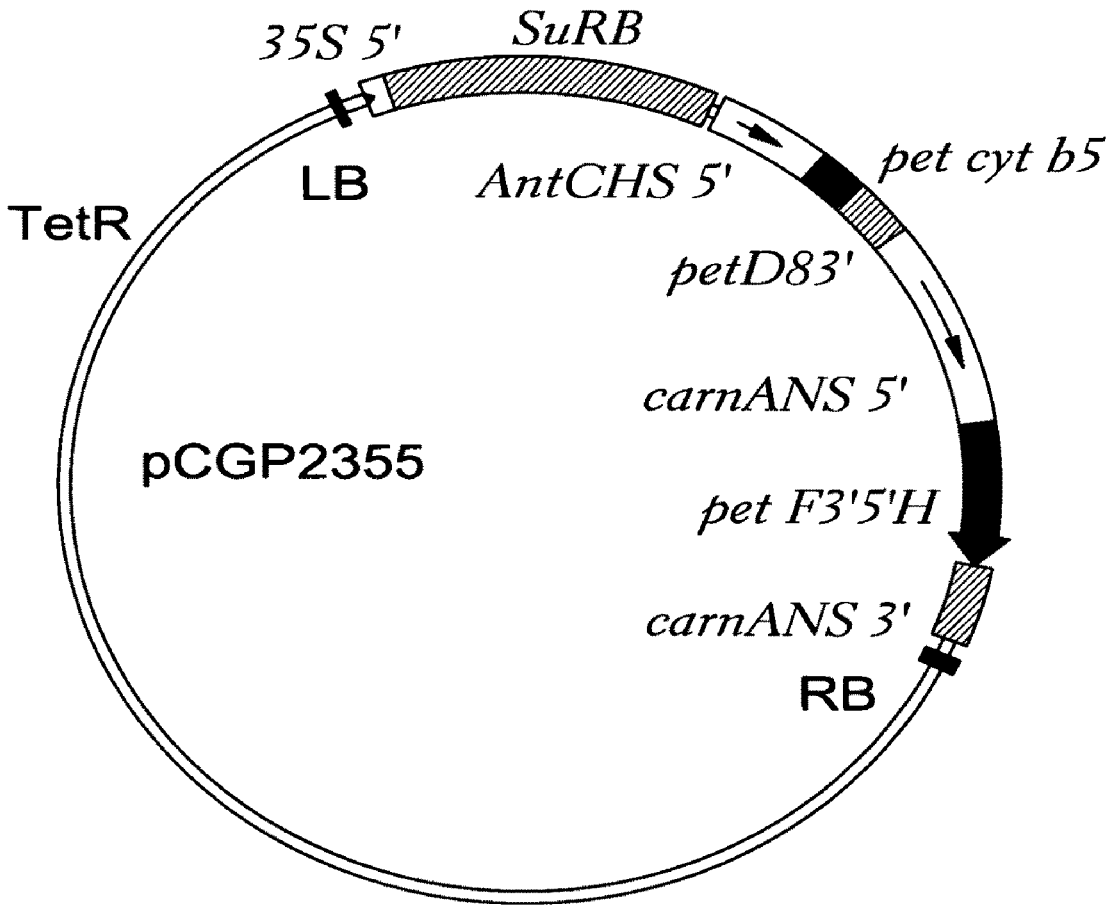
FIG. 2 is a diagrammatic representation of the binary plasmid pCGP2355. Selected restriction endonuclease sites are marked. Abbreviations include LB =Left Border from *A. tumefaciens* Ti plasmid, RB =Right border region from *A. tumefaciens* Ti plasmid, TetR =antibiotic, tetracycline resistance gene complex.

The new variety was originally selected in vitro as a regenerated shoot from a 'Cerise Westpearl' carnation meristematic cell that had been transfected with *Agrobacterium tumefaciens* AGL0 (Lazo et al, Bio/technology 9:963-967, 1991) carrying the plasmid pCGP2355 (FIG. 2). The new variety differs from the 'Cerise Westpearl' parent in that its average crop time is 167 days versus 174.7 days for the parent; its internode length averages 73.4 mm versus 81.6 mm for the parent; its average number of petals is 35 versus 44.7 for the parent; its ground color of blade and color of band around the center is N78A versus 58B for the parent; and its average number of stamen is 12.3 versus 10.3 for the parent. The new variety also differs from other known *dianthus* cultivars, such as 'FLORIAMETRINE' and'FLORIAGATE'. For example, the new variety has a crop time of about 167 days, whereas 'FLORIAMETRINE' has an average crop time of about 107 days. The new variety has a node color of about 192D whereas 'FLORIAGATE' has a node color of about 192A. The leaf dimension of the new variety are about 49.7 mm by about 6.3 mm, whereas the leaf dimension of 'FLORIAMETRINE' are about 40.5 mm by about 7 mm and the leaf dimensions of 'FLORIAGATE' are about 53.9 mm by about 6.6 mm.

Asexual reproduction of the new cultivar was first accomplished in 2007 in a cultivated area of Bundoora, Victoria, Australia. The method of asexual propagation used was vegetative cuttings. Since that time the characteristics of the new cultivar have been determined stable and are reproduced true to type in successive generations of asexual reproduction.

BOTANICAL DESCRIPTION OF THE PLANT

The following is a detailed description of the new cultivar 'FLORIJADE'. Data was collected from plants grown indoors in Bundoora, Victoria, Australia. The Royal Horticultural Society's Colour Charts, Third and/or Fifth edition (London, UK), 1995 and/or 2007 were used to provide a description of observed color, except where general color terms of ordinary dictionary significance are used. Growing conditions are typical to other species, sports, and lines of *Dianthus*.

Botanical classification: *Dianthus caryophyllus*.

Species: *Caryophyllus*.

Common name: Carnation.

Commercial classification: *Dianthus caryophyllus* 26407.

Type: *Herbaceous perennial.*

Use: Used as a flowering plant for pots and containers.

Parentage: 'FLORIJADE' is a transgenic plant that resulted from the transformation of *D. caryophyllus* cultivar 'Cerise Westpearl' as disclosed in paragraph [0025] with the transformation vector, pCGP2355.

TABLE 1

| Plant Description | |
|---|---|
| Bloom period | All year |
| Plant habit | Spray type carnation |
| Plant height | Average plant height at flowering - 926.4 mm |
| Plant width | 150 to 180 mm at flowering |
| Plant hardiness | Not tested for hardiness |
| Root system | Fine fibrous root system |
| Propagation | Vegetative propagation |
| Cultural requirements | Grown hydroponically in a greenhouse. Plants fertilized via drip irrigation system. |
| Pests and diseases | Susceptible to known *Dianthus* pest and diseases |
| Time and Temperature needed to produce a rooted cutting | 3 to 4 weeks to produce rooted cuttings, bench heat: 18-22° C., Air temp approx. 15 to 22° C. |
| Crop time | Average days to flowering: 167. |
| Stem shape | Cylindrical, Ave stem diameter at 5th node: 7.8 mm |
| Stem surface | Glabrous and glaucous |
| Stem color | 137B |
| Branching | Little branching from the axils of lower leaves |
| Internode length | Average length of 5th internode: 73.4 mm |
| Node color | 192D |
| Node dimensions | 6 mm diameter and 3 mm in length |

TABLE 2

| Foliage | |
|---|---|
| Type | Evergreen |
| Shape | Linear |
| Division | Simple |
| Apex | Acute |
| Base | Decurrent |
| Venation | Not prominent |
| Margins | Entire |
| Attachment | Sheathing |
| Arrangement | Opposite and spiraling up stem |
| Surfaces (upper and lower) | Glaucous |
| Leaf dimensions | 3rd leaf from flower, Ave length: 49.7 mm, Ave width: 6.3 mm |
| Leaf color (upper and lower) | 137A |
| Fragrance | Absent |

TABLE 3

| Flowers | |
|---|---|
| Inflorescence | Cymose |
| Flower type | Saliform,double and symmetrical |
| Flower dimensions (including calyx) | Ave corolla height: 30.3 mm, Ave calyx height: 29 mm |
| Fragrance | Absent |
| Bud color | 191B |
| Anthocyanin | Present |
| Bud dimensions | Ave bud length: 24.5 mm, Ave bud width: 11.2 mm |
| Bud shape | Cylindrical |
| Petals | Persistent, apopetalous, overlapping |

TABLE 3-continued

| Flowers | |
|---|---|
| Petal number | Ave number of petals: 35 |
| Petal margin | Crenate-dentate |
| Petal shape | Obteltoid |
| Petal surface | Glabrous |
| Petal dimensions | Ave petal length: 50.1 mm, Ave petal width: 26.2 mm |
| Ground color of blade | N78A |
| Color of band around centre | N78A |
| Color of middle of strap | 145D |
| Color of base of strap | 145D |
| Calyx dimensions | Ave calyx length: 29 mm, Ave calyx diameter at apex: 16.4 mm |
| Calyx color | 143A |
| Anthocyanin | Absent |
| Sepals | Ave number of sepals: 6 |
| Fused or Unfused | Unfused |
| Sepal color | 143A |
| Anthocyanin | Absent |
| Peduncle dimensions | Ave peduncle length: 34.1 mm, Ave peduncle width: 2.3 mm |
| Peduncle color | 138A |
| Peduncle surface | Glaucous |
| Epicalyx | Present |
| Bracts | 1 pair in number (2 individual bracts) |
| Bracts dimensions | 2 mm × 28 mm |
| Bract color | 138A |
| Anthocyanin | Absent |
| Bracteoles | 1 or 2 pair(s) |
| Dimensions | 2 mm × 18 mm |
| Anthocyanin | Absent |
| Stipules | Absent |
| Stipules dimensions | N/A |
| Stipule color | N/A |
| Anthocyanin | N/A |
| Lastiness of flowers | Not tested |

TABLE 4

| Reproductive Organs | |
|---|---|
| Stamens | Ave number of stamens: 12.3 |
| Stamen dimensions | Ave length of stamen: 18.3 mm |
| Stamen color | N155B |
| Anther number | Ave of normal anthers: 1.1, Ave of abnormal anthers: 6.2 |
| Anther attachment | Dorsifixed |
| Anther color | 156D |
| Anther dimensions | Ave anther length: 1.45 mm, Ave anther width: 0.48 mm |
| Pollen | Little pollen |
| Pistil | One that divides into 2 above the ovary |
| Pistil dimensions | Average pistil length: 34.2 mm |
| Styles | Average No: 2, Average length: 25.4 mm |
| Style color | 155A |
| Stigma number | Single |
| Stigma shape | A single stigma |
| Stigma color | 155A |
| Height above petals | Stigma does not protrude above petals |
| Ovary position | Superior |
| Ovary dimensions | Ave ovary height: 8.7 mm, Ave ovary width: 6.3 mm |
| Ovary shape | Obovoid |
| Ovary color | Upper: 145A, Lower: 155A |
| Seed | Absent |

The *Dianthus* 'FLORIJADE' is now described by the following non-limiting Examples.

EXAMPLE 1

Generation of *Dianthus* 'FLORIJADE'

In order to increase the levels of delphinidin-based anthocyanins and therefore increase the chance of violet/purple/blue color in the Cerise Westpearl spray carnation flowers, a construct (pCGP2355) was prepared that included the use of a F3'5'H gene and a cyt b5 gene.

The F3'5'H coding sequence in the chimeric gene (carnANS 5': pet F3'5'H: carnANS 3') used in the construct pCGP2355 was from petunia.

The cytochrome b5 coding sequence used in the the chimeric gene (AmCHS 5': pet cytb5: petD8 3') used in the construct pCGP2355 was from petunia.

Preparation of the transformation vector, pCGP2355

The transformation vector pCGP2355 (FIG. 2) contains the carnANS 5': pet F3'5'H: carnANS 3' expression cassette along with a AmCHS 5': pet cytb5: petD8 3' expression cassette and the 35S 5': SuRB selectable marker gene.

Agrobacterium tumefaciens strains and transformations

The disarmed *Agrobacterium tumefaciens* strain used was AGL0 (Lazo et al, 1991 supra).

Plasmid DNA was introduced into the *Agrobacterium tumefaciens* strain AGL0 by adding 5 μg of plasmid DNA to 100 μL of competent AGL0 cells prepared by inoculating a 50 mL LB culture (Sambrook et al, Molecular Cloning: A Laboratory Manual, Cold Spring Harbor Laboratories, Cold Spring Harbor, N.Y., USA, 1989) and incubating for 16 hours with shaking at 28° C. The cells were then pelleted and resuspended in 0.5 mL of 85% (v/v) 100 mM $CaCl_2$/15% (v/v) glycerol. The DNA-Agrobacterium mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1mL of LB (Sambrook et al, 1989 supra) media and incubated with shaking for 16 hours at 28° C. Cells of *A. tumefaciens* carrying the plasmid were selected on LB agar plates containing appropriate antibiotics such as 50 μg/mL tetracycline. The confirmation of the plasmid in *A. tumefaciens* was done by restriction endonuclease mapping of DNA isolated from the antibiotic-resistant transformants.

Plant transformations were as described in International Patent Application No. PCT/US92/02612 or International Patent Application No. PCT/AU96/00296 or Lu et al, Bio/Technology 9: 864-868, 1991, each of which are incorporated herein by reference.

Cuttings of *Dianthus caryophyllus* cv. Cerise Westpearl were obtained from Queensland, Australia.

EXAMPLE 2

Figure 3:
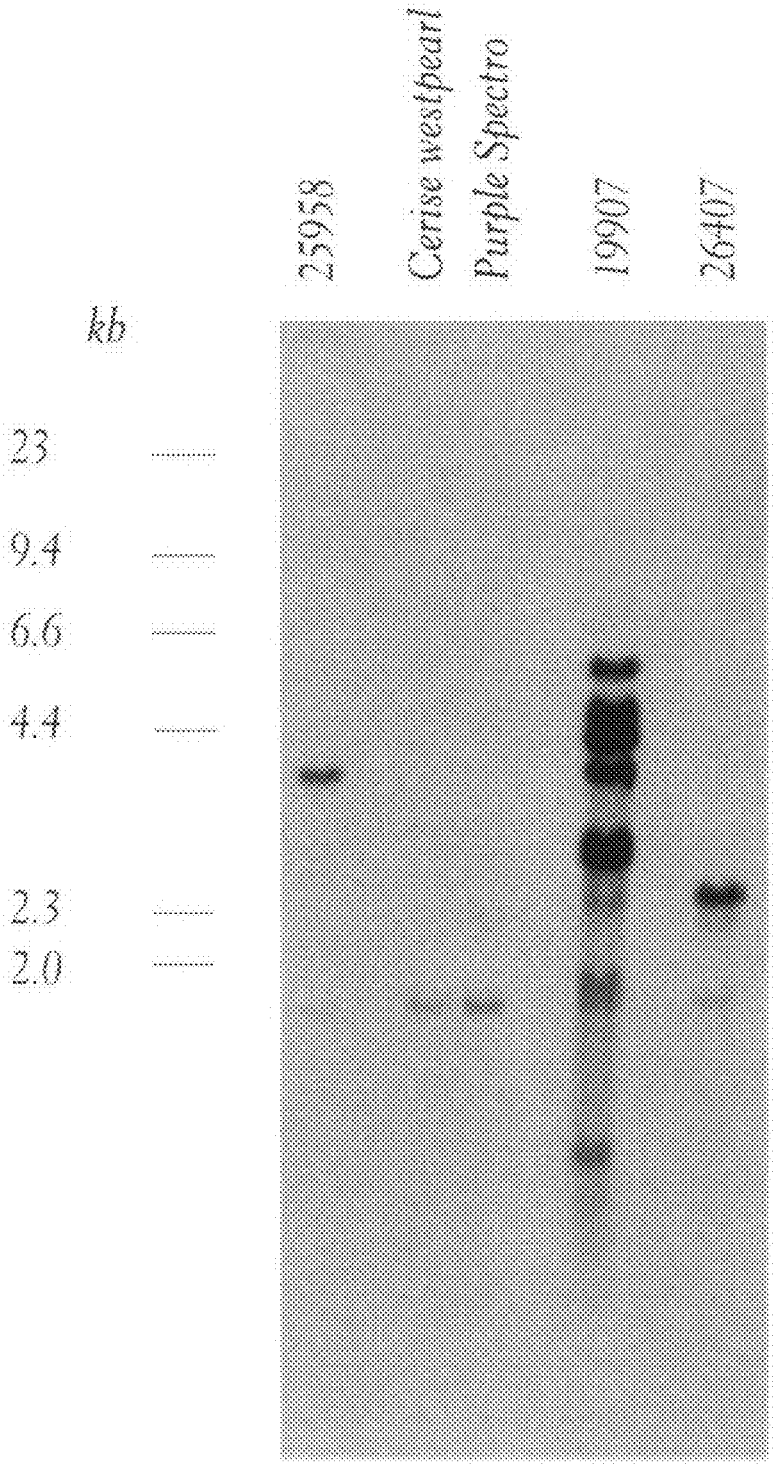
FIG. 3 is a photographic representation of a high resolution scan of a Southern blot autoradiograph showing 10 μg of EcoRI-treated genomic DNA from the transgenic carnation line 26407 ('FLORIJADE'), in comparison to 10 μg of EcoRI-treated genomic DNA from the carnation lines Cerise Westpearl, Purple Spectro, and the transgenic carnation lines 19907 ('FLORIAMETRINE') and 25958 ('FLORIAGATE'), hybridized with the NtALS probe.

Detection of the SuRB chimeric gene from the transformation vector pCGP2355 in *Dianthus* 'FLORIJADE' plants In order to determine stable transformation of *Dianthus caryophyllus* with the T-DNA from the transformation vector pCGP2355, transgenic plants were analyzed by Southern blot. The results are shown in FIG. 3.

Preparation of genomic DNA and Southern analysis

Genomic DNA was isolated from leaf tissues as described by Dellaporta et al, Molecular Biology Reporter 1(14):19-21, 1983. The genomic DNA (10 μg) was digested for 48 hours using 120 units of the restriction endonuclease EcoRI at 37° C. DNA fragments were separated by electrophoresis through a 0.8% w/v agarose gel. The DNA was transferred to Hybond NX membrane (Amersham) as described (Sambrook et al, 1989 supra).

The following samples were analyzed:

1. HindIII-treated λDNA standard markers (size range: 23.13, 9.42, 6.56, 4.36, 2.32, 2.03 kb),
2. 10 μg of EcoRI-treated genomic DNA from transgenic carnation line, 25958 ('FLORIAGATE'),
3. 10 μg of EcoRI-treated genomic DNA from non-transgenic carnation parental line, Cerise Westpearl,
4. 10 μg of EcoRI-treated genomic DNA from non-transgenic carnation line, Purple Spectro,
5. 10 μg of EcoRI-treated genomic DNA from transgenic carnation line, 19907 ('FLORIAMETRINE'), and
6. 10 μg of EcoRI-treated genomic DNA from transgenic carnation line 26407 ('FLORIJADE').

Following electrophoresis, the gel was prepared for blotting by a 15 minutes depurination step in 0.25 M HCl, two 20 minute washes in denaturing solution (1.5 M NaCl, 0.5 M NaOH) and two 20 minute washes in neutralization solution (0.5 M Tri-HCl, pH 7.5, 0.48 M HCl, 1.5 M NaCl). DNA was capillary transferred to Hybond-NX nylon membrane (Amersham Biosciences, UK) in 20×SSC (3 M NaCl, 0.3 M Tris-Na citrate, pH 7.0).

Preparation of probes

A probe corresponding to a 770 bp fragment of the ALS (acetolactate synthase) gene from *Nicotiana tabacum* (NtALS) was used for Southern blot analysis. The probe fragment was originally generated by PCR and subsequently sub-cloned into an amplification vector (pBluescript II, Stratagene, USA), given a reference number (pCGP1651) and the fragment sequenced. After confirmation of the correct sequence, the DNA fragment was isolated from the source plasmid using the restriction endonuclease HindIII. The fragment was separated by 1% w/v agarose gel electrophoresis and purified using the MinElute Gel Extraction kit and protocol (Qiagen, Australia).

32P-Labeling of DNA Probes

DNA fragments (25-50 ng) were labeled with 50 μCi of [α-32P]-dCTP (PerkinElmer Life and Analytical Sciences, USA) using a Decaprime kit (Ambion, USA). Unincorporated [α-$^{32}$P]-dCTP was removed by chromatography on Sephadex G-50 (Fine) columns. The labeled probe fragment was counted using a BioScan radioisotope counter (QC:4000 XER, BioScan, USA).

Hybridization and Detection

Membranes were pre-hybridized in 10 mL hybridization buffer (50% v/v deionized formamide, 1 M NaCl, 1% w/v SDS, and 10% w/v dextran sulfate) at 42° C. for 1 hour. Once denatured, 10,000,000 dpm of 32P-labeled probe was added to the hybridization solution and hybridization was continued at 42° C. for a further 16 hours. Membranes were washed twice in low stringency buffer (2×SSC, 1% w/v SDS) at 65°

C. for 30 minutes. Membranes were exposed to Kodax BioMax MS X-Ray film (Kodak, USA) with an intensifying screen at −70° C. for 16 hours. The exposed films were automatically developed using a Curix 60 X-ray developer (AGFR-Gevaert Group, Belgium).

What is claimed is:

1. A new and distinct cultivar or *Dianthus* plant named 'FLORIJADE' as described and illustrated herein.

* * * * *